United States Patent [19]

Solomonow

[11] Patent Number: 4,781,180
[45] Date of Patent: Nov. 1, 1988

[54] ORTHOTIC KNEE BRACE SYSTEM AND METHOD

[76] Inventor: Moshe Solomonow, 3380 State St. Dr., New Orleans, La. 70125

[21] Appl. No.: 909,899

[22] Filed: Sep. 22, 1986

[51] Int. Cl.$^4$ .............................................. A61F 5/00
[52] U.S. Cl. ................................. 128/80 C; 128/80 F
[58] Field of Search ................ 128/80 C, 80 F, 80 H, 128/80 R, 88

[56] References Cited

U.S. PATENT DOCUMENTS

| | | | |
|---|---|---|---|
| 1,114,389 | 10/1914 | Semeleder | 128/80 H |
| 2,477,591 | 8/1949 | Follis | 128/80 H |
| 2,883,982 | 4/1959 | Kaney | 128/80 C |
| 4,428,369 | 1/1984 | Peckham et al. | 128/80 C |
| 4,617,920 | 10/1986 | Carsalade | 128/80 C |
| 4,649,906 | 3/1987 | Spademan | 128/80 C |
| 4,655,201 | 4/1987 | Pirmantgen | 128/80 C |

*Primary Examiner*—Edgar S. Burr
*Assistant Examiner*—Tonya Lamb
*Attorney, Agent, or Firm*—Harry B. Field

[57] ABSTRACT

An improved orthotic knee brace system for single and multiple posterior, anterior and lateral knee injuries includes first and second depending frameworks for attaching around a human leg, respectively, above and below the knee joint, the frameworks being hingedly interconnected for relative movement during walking. One of the frameworks bears a cammed surface adjacent the other framework, which other framework has a tibia-stabilizing force transfer mechanism in the form of a lever pivoted thereto. One arm of the lever bears an adjustable contact member adapted to contact the cammed surface, while another arm of the lever is pivotably connected to a tibia-bracing component adapted to wrap around the lower leg portion to prevent tibial displacement during knee movement, as in walking. Preferably, each framework has depending side strips connected to wrap-around leg straps, and the strips of one framework have offset members bearing the cammed surfaces. Multiple sets of the frameworks and tibia-stabilizing force transfer mechanisms can be positioned around the leg to correct multiple knee injuries. The system and its method of use are simple and effective.

14 Claims, 2 Drawing Sheets

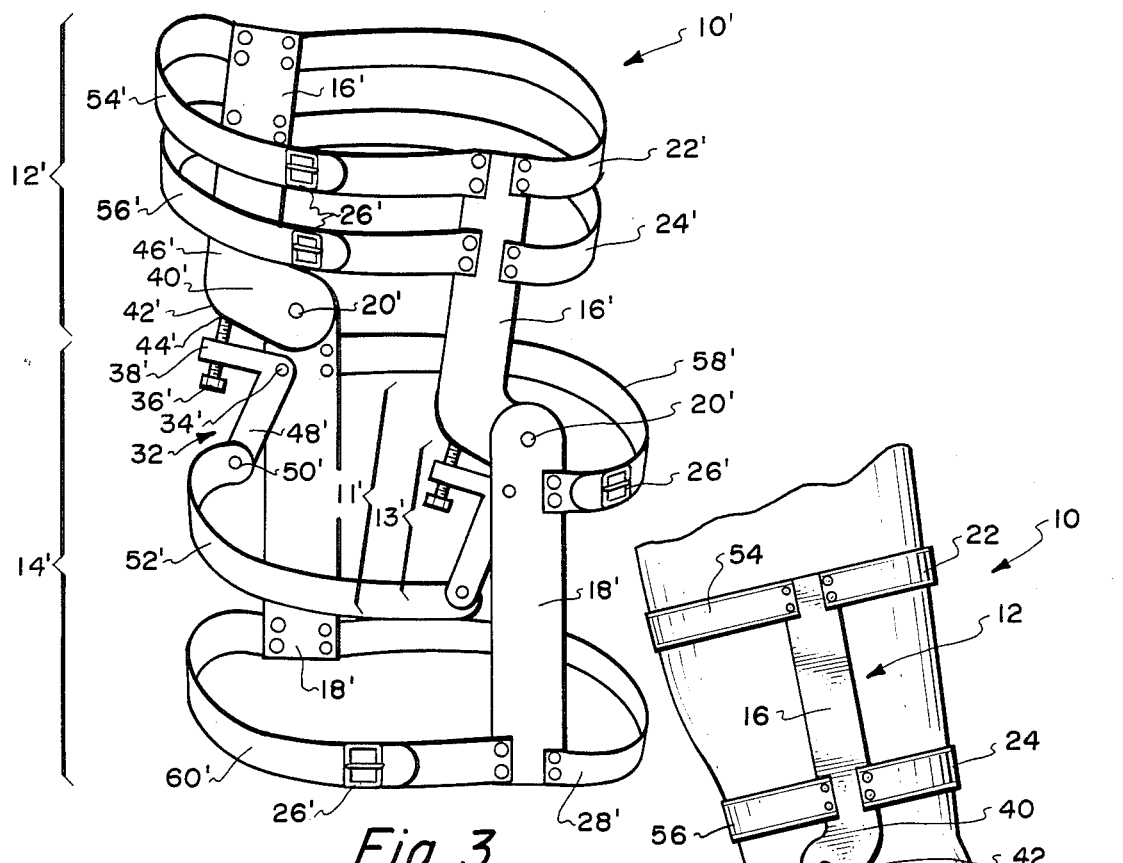
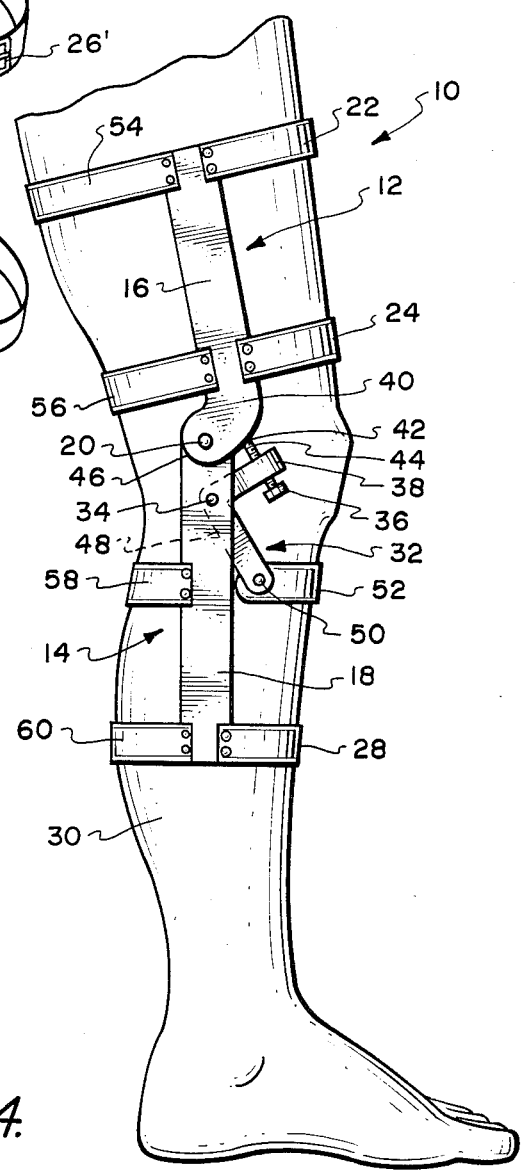
Fig. 3.
Fig. 4.

ORTHOTIC KNEE BRACE SYSTEM AND METHOD

BACKGROUND OF INVENTION

1. FIELD OF THE INVENTION

The present invention relates generally to the orthotic field and, more particularly, to orthotic knee braces used by patients suffering a deficiency of the knee function due to injuries of the ligaments or connective tissues.

2. PRIOR ART & GENERAL BACKGROUND

Several knee braces intended to provide a stabilizing function to an injured knee are described in the prior art. Such braces usually provide rigid mechanical-limiting stops to prevent the knee from hyperextension or to provide some elastic force to counter the knee's extension forces. A more recent approach includes a pneumatic enclosure of the knee that creates a large amount of mechincal opposition to both flexion or extension, which, however, causes severe limitation of movement and therefore is not wholly desireable.

For typical prior art approaches, see U.S. Pat. No. 4,397,308 involving the so-called Dynasplint System, U.S. Pat. No. 4,407,276 and U.S. Pat. No. Des. 269,379. Note also Lew, William D., M.S., et al., *Orthotics and Prosthetics,* "A Comparison of Pistoning Forces in Orthotic Knee Joint," Vol. 36, No. 2, Summer 1982, pp. 85-95; Lewis, Jack L., Ph.D., et al., *Orthotics and Prosthetics,* "A New Concept in Orthotics Joint Design—The Northwestern University Knee Orthosis System," Vol. 37, No. 4, Winter 1983-84, pp. 15-23; and Lewis, Jack L., Ph.D., et al., Orthotics and Prosthetics, "A New Concept in Orthotics Joint Design—The Northwestern University Knee Orthosis System Part II: The Complete Orthosis," Vol. 38, No. 1, Spring 1984, pp. 13-28. Further, see U.S. Pats. Nos. 4,337,764 ("ZINCO"); and 4,280,489. See also U.S. Pat. Nos. 3,955,565 and 4,361,142.

Such prior art devices, if they provide any interaction at all to prevent knee joint dislocation, typically severaly limit the range of motion of the leg of the patient, and thus are undesireable.

Since most of the ligaments, cartilage or connective tissue of the knee which is injured and/or subsequently removed provides a natural retaining action to the knee's bones during knee and leg movement and flexion or extension, it is necessary and desireable to provide such retaining action in an orthotic knee brace, without severely limiting the natural range of movement of the knee and leg. This has not been provided by any known prior art knee brace. It is also necessary to require the terminal angular velocity during extension or flexion to that which will not induce displacement of the joint bones relative to each other when the leg is fully extended or flexed.

A substantial difference between the retaining action generated by the system of the present invention compared to that of the devices of the prior art which severely limit the range of motion is the prevention of the terminal impact, which is present in prior art devices. Such terminal impact is transfered to the tissue, causing excessive pressure, discomfort and skin laceration. The present invention, by virtue of not limiting the range of motion, also allows the user to maintain normal movement patterns of the knee and leg without imposing on the wearer the necessity of having to modify his or her walking pattern as do prior art devices. Those prior art devices cause the wearer to work in a disadvantageous manner and substantially increase the demands upon the legs muscles, causing premature fatigue and general increase in metabolic energy expenditure.

An important advantage of providing the retaining force to the knee, a with the present device, while undergoing the necessary extremes of range of motion is that such retaining force satisfies the equilibrium of the joint, substituting for the lost retaining force of the injured ligament as described by P. Renstrom, et al. *American Journal of Sports Medicine,* Vol. 14, No. 1, pages 83-87, 1986, in particular as shown in FIGS. 3, 4, 5 and 6 of that publication.

Such equilibrium could be described by the equation as follows in the case of extension $$\vec{F_Q} = \vec{F_L} + \vec{F_{EL}}$$

or, quadriceps muscle force = ligament force + external load.

When the ligament is injured or removed, equilibrium is disturbed, causing the displacement of the bones, which can be prevented if the ligament retaining force is substituted for by the leverage mechanism retaining force described in the present invention.

SUMMARY OF THE INVENTION

The improved orthotic knee brace system and method of use of the present invention satisfy the foregoing needs. The system and method are substantially as described in the Abstract. Thus, the primary objective of this invention is to provide a device which effectively substitutes for the lost retaining force of the injured ligaments of the knee during knee movement and which maintains the knee's stability in the anterior-posterior orientation. Preferably, the present device allows complete extension or flexion, so that limitation of the range of motion of the knee and leg is not necessary.

The present system can provide retaining force to the knee in specific segments of the movement, such as in near full extension or near full flexion, or any other segment as may be necessary and can provide retaining force to the injured knee with a full range of normal motion without introducing any high velocity impact, with resulting vibration, instability and strain on the joint. The system also provides an adjustable mechanism which activates the leverage mechanism of the system in the most preferable segment of motion as may be needed for various individuals according to their weight, size, age, physical conditioning, athletic activity, etc.

In the preferred embodiment of the present system, a rigid full range of motion knee brace is provided with a joint-retaining leverage mechanism that acts to stabilize the tibia during knee and leg action so that normal walking can be carried out.

Other features of the improved system of the present invention are set forth in the following detailed desription and accompanying drawings.

DRAWINGS

FIG. 3 is a perspective view of the posterior joint retainer knee orthotic system of the present invention.

FIG. 4 is a schematic side view showing the system of FIG. 1 in place on a patient's leg, providing its protective and remedial action during a leg extension movement of the patient, the patient having an anterior cruciate ligament injury.

The same elements or parts throughout the figures of the drawing are designated by the same reference characters, while equivalent elements bear a prime or double prime designation.

DETAILED DESCRIPTION OF THE INVENTION

Figure 1:
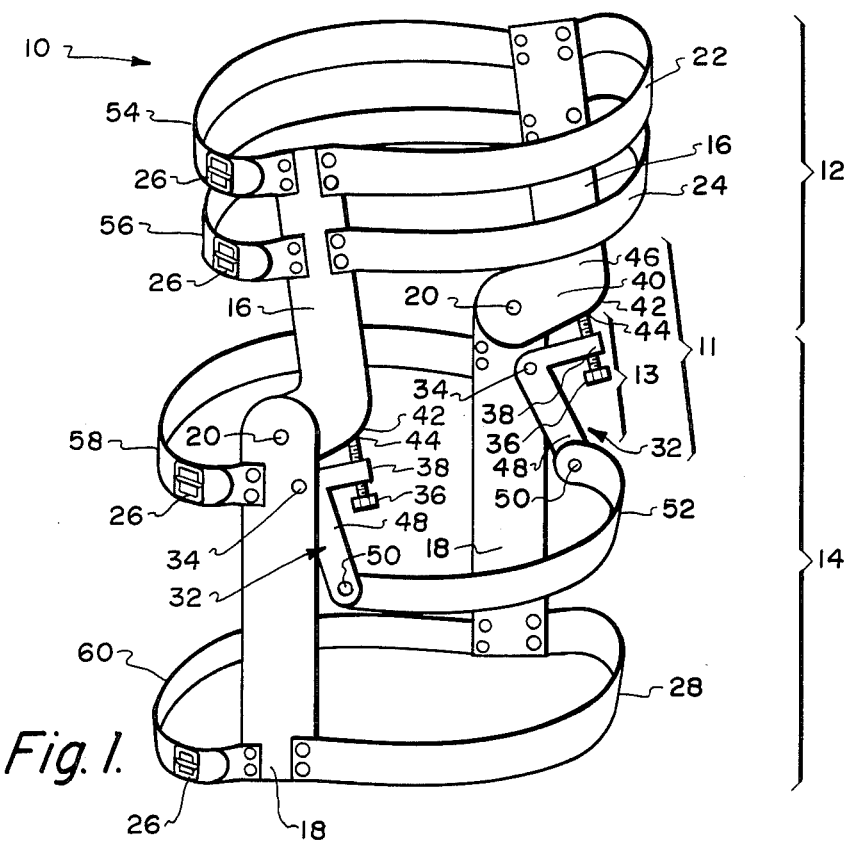
FIG. 1 is a perspective of the anterior joint retainer knee orthotic system of the present invention.

Now referring more particularly to FIG. 1, there is schematicaly shown a persepctive view of the anterior configuration of joint retainer knee orthotic system generally designated 10. Anterior system 10 is designed to apply increasing posteriorly directed pressure to the upper anterior portion of the tibia as the wearer's leg extends from a bent fixed to the fully extended position thereby preventing the anterior dislocation of the tibia from the knee joint. To effect this novel restraining pressure on the wearer's tibia, anterior system 10 relies upon the interaction of upper framework generally designated 12 and depending lower framework generally designated 14 through the tibia stabilizing force transfer assembly generally designated 11. Frameworks 12 and 14 made up of depending, rigid, preferably metal members or strips 16 and 18, respectively, pivotally joined together by a concentric pivot or hinge 20. Alternatively, the hinge could be polycentric, offset or any combination thereof. A set of depending rigid members identical to members 16 and 18 can, as shown in FIG. 1, be provided on the opposite side of the user's leg as part of frameworks 12 and 14.

Spaced rigid and/or elastic straps or supports 22, 24, and 28 which are preferably individually fitted to the patient's anatomy, are attached to strips 16 and 18, as shown in FIG. 1, and extend anteriorly and orthogonally therefrom to wrap around the patient's leg 30 (FIG. 4). Supports 22, 24, and 28 can be, for example, in the form of elastic, metal and/or plastic straps. Flexible or elastic straps 54, 56, 58 and 60 are provided to tightly secure and attach system 10 to leg 30 by means of a connector 26. Although connector 26 is shown as a buckle, any other connector such as Velcro or a tie would also work.

A force transfer mechanism generally designated 13 comprises an L-shaped lever generally designated 32 and an adjustable contact member preferably a screw plunger 36. Although the dual-sided device of FIG. 1 is preferred, a single-side device of FIG. 2 could also work. L-shaped lever 32 is pivotally connected to the upper end of strip 18 by a hinge 34. A contact member in the form of a screw plunger 36 is threadably attached to upper lever arm 38 and adjustably extends up therefrom. Thus, it can be adustably threaded up and down so as to adjust the range of motion in which lever arm 38 engages framework 12 to thereby generate a tibia retaining force. Although lever 32 is preferred to be L-shaped, other geometric configurations could also provide the desired force transfer.

Figure 2:
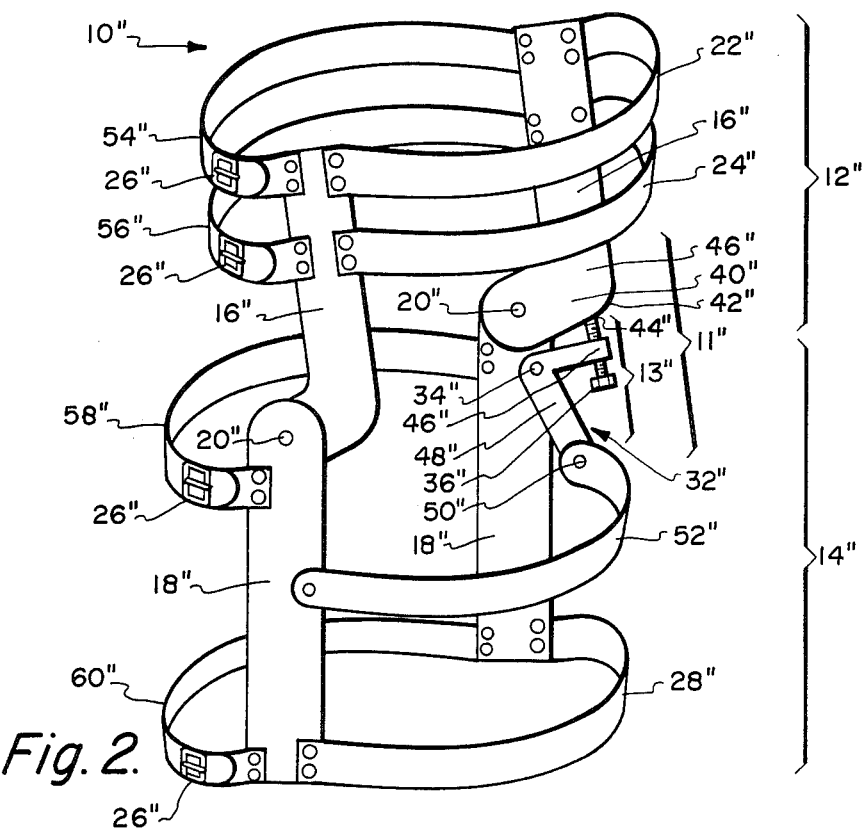
FIG. 2 is a perspective view of the anterior joint retainer knee orthotic system showing a single force transfer mechanism.

As can be seen in FIG. 1, the bottom portion 40 of strip 16 has a cammed surface 42 against which the upper tip 44 can bear. In FIGS. 1 and 2, strip 16,16" is offset forwardly of strip 18,18" and then extends rearwardly to form offset 46,46" thereby causing cammed surface 42,42" to project forward of strip 18,18" as does lever arm 38,38". In FIG. 3, the posterior configuration 10' is depicted. As can be seen in FIG. 3 anteriorly directed tibia retaining force is applied to the upper posterior portion of the tibia in the reverse manner as described in regard to anterior configuration 10. Thus strip 16' is offset rearwardly of strip 18' so that cammed surface 42' projects rearward of lower strip 18' as does lever arm 38'.

Specifically, FIG. 3 shows the posterior configuration of joint retainer knee orthotic system generally designated 10'. Where anterior system 10 was designed for assisting a wearer who had suffered anterior ligament injuries, posterior system 10' is designed for use in situations where posterior ligament injuries have occurred. Thus, posterior system 10' is the reverse of system 10 and operates so that cammed surface 42' and lever 32' extend posteriorly and apply increasing anteriorly directed pressure to the upper posterior portion of the tibia as the wearer's leg flexes from an extended to the fully flexed position. This increasing anterior pressure thus prevents the posterior dislocation of the tibia from the knee joint at full leg flexion. The specific operation of posterior system 10' will be more fully described below concurrent with the operational description of anterior system 10 and 10". It should also be noted that the system 10" depicted in FIG. 2 also operates in a similar manner.

As upper framework 12,12',12" pivots about concentric hinge 20,20',20" cammed surface 42,42',42" engages tip 44,44',44" of screw plunger 36,36',36" and transfers the developed forces from the extension or flexion movement of the knee to lever 32,32',32" through arm 38,38',38" thereby creating a certain torque around hinged 34,34',34". The created torque is further transferred via lower lever arm 48,48',48" which is connected by a hinge 50,50',50" to a rigid or elastic tibia retaining strap 52,52',52" which is wrapped around the patient's tibial bone just below the knee. Tibial retaining strap 52,52',52" can be made of a molded rigid material to fit the anatomy, or of an elastic material that may provide elastic retaining force of varying degrees in cases of moderate to mild injuries, if preferred.

The torque transmitted via lever arm 48,48',48" and hinge 50,50',50" is transformed by strap 52,52',52" into a retaining force which compresses the proximal aspect of the tibial bone posteriorly in the anterior configuraton 10 and 10" anteriorly in the posterior configuraton 10', thereby preventing its dislocation during the terminal phase of leg extension and flexion, respectively.

With the described components, the relative movements between the two frameworks 12,12',12" and 14,14',14" are sensed and the desired tibial retaining force is always generated and transferred to the tibial bone via lever 38,38',38" hinge 50,50',50" and tibial retaining strap 52,52',52".

Although FIG. 4 depicts anterior system 10,10" the below description applies equally to posterior system 10'. As can be seen in FIG. 4, when present system 10,10',10" is placed on the leg 30 of the patient, straps 22,22',22",24,24',24", and 28,28',28" are used which can be part elastic, such as rear portions 54,54',54",56,56',56", 58,58',58" and 60,60',60", while the remainder may be molded plastic or the like. Thus, portions 54,54',54", 56,56',56", 58,58',58", and 60,60',60" are used to fasten system 10,10',10" to leg 30 of the patient, while the remainder of supports 22,22',22", 24,24',24", and 28,28',28" act as femural and tibial retainers. As the patient walks or otherwise extends or flexes the knee joint, upper framework 12,12',12" pivots relative to the lower framework 14,14',14" causing screw plunger 36,36',36" to engage cammed surface 42,42',42" during the desired phase of the movement and to develop tibial retaining forces to the joint, which otherwise would have been absent due to the patient's ligament injury. In use, system 10,10" provides tibial retaining force during the terminal extension phase of movement and system 10' provides tibial retaining force during the terminal flexion phase of movement. Adjustable regulation of the duration of the terminal extension phase as may be needed for individuals of different physical attributes, severity of injury and athletic activity is provided by threaded adjustment of the position of tip 44,44',44" of screw plunger 36,36',36".

The present method comprises orthotically treating a patient by installing the present system, such as is exemplified by system 10 on the patient, as shown in FIG. 4, and allowing the two frameworks and force-transferring mechanism to provide a tibial-retaining action for the knee joint during its movement so that such movement is comparable to that of a healthy joint.

As can be seen from the above, the present system has unique advantages over prior knee brace devices, and is simple, durable, efficient and inexpensive. It permits the patient to duplicate normal movement without any undesirable side effects, while providing full support. Other advantages are set forth in the foregoing.

Various modifications, changes, alterations and additions can be made in the present system, its components and parameters. All such modifications, changes, alterations and additions as are within the scope of the appended claims form part of the present invention.

What is claimed is:

1. An anterior orthotic knee brace system for gradually providing and increasing a posteriorly directed retaining force to the upper anterior portion of the tibial bone as wearer's leg extends and wherein said system comprises in combination:
   (a) a first framework, including means for attaching said framework to a human leg above the knee joint.
   (b) a second framework, including means for attaching said framework to a human leg below the knee joint.
   (c) hinge means for pivotally interconnecting said first and second framework, and
   (d) a tibia stabilizing force-transfer assembly operatively interconnected between said first and second frameworks, said force-transfer assembly including means for gradually increasing the posteriorly directed retaining force at the upper anterior portion of the tibia as the leg extends thereby preventing anterior dislocation of the tibia from the knee joint.

2. The anterior orthotic knee brace system of claim 1 wherein said tibia stabilizing force-transfer assembly includes:
   (1) a cammed surface secured to said first framework and posititioned adjacent to said second framework, and
   (2) a force-transfer mechanism pivotally secured to said second framework, including a lever having first and second lever arms and an adjustable contact member and wherein said first lever arm is adjacent said cammed surface and carries said adjustable control member adopted to bear against said cammed surface during relative knee movement, and a tibia retaining strap pivotally connected to said second lever arm, whereby the force applied to said first lever arm through said cammed surface during knee movement is transferred by said second lever arm to said tibia retaining strap to prevent anterior dislocation of said tibia at full leg extension.

3. The anterior orthotic knee brace system of claim 2 wherein said first and second frameworks each include depending side strips orthogonally connected to straps adapted to wrap around the respective upper and lower leg portions, said depending side strips being hingedly interconnected, said side strips of said first framework each being generally forwardly displaced from said side strips of said second framework and wherein said side strips of said first framework further comprise rearwardly-extending offset end member having said cammed surface.

4. The anterior orthotic knee brace system of claim 3 wherein said side strips of said first framework are anteriorly displaced from said side strips of second framework by said offset end members through which said frameworks are pivotably connected, and wherein said ever is generally L-shaped, said contact-member comprising a screw plunger threaded through said upper lever arm.

5. The anterior orthotic knee brace system of claim 4 wherein said tibia retaining strap is adapted to bear against the tibia to prevent its displacement during leg movement.

6. The anterior orthotic knee brace system of claim 5 wherein said cammed surface is located forwardly of said second framework strips and wherein said lever arms also extend forwardly of said second framework strips to treat anterior knee injuries.

7. The anterior orthotic knee brace system of claim 2 wherein said system includes a pair of said first and second side strips located one pair each on either side of said anterior orthotic knee brace system and wherein both pairs further include said force transfer mechanism.

8. A posterior orthotic knee brace system for providing and gradually increasing an anteriorly directed retaining face to the upper posterior portion of the tibial bone as wearer's leg flexes and wherein said system comprises in combination:
   (a) a first framework, including means for attaching said framework to a human leg above the knee joint,
   (b) a second framework including means for attaching said framework to a human leg below the knee joint,
   (c) hinge means for pivotally interconnecting said first and second framework, and
   (d) a tibia stabilizing force-transfer assembly operatively interconnected between said first and second frameworks, said force-transfer assembly including means for gradually increasing the anteriorly directed retaining force at the upper posterior portion of the tibia as the leg begins flexion with the retaining reaching a maximum as the leg reaches full flexion thereby preventing posterior dislocation of said tibia from the knee joint.

9. The posterior orthotic knee brace system of claim 8 wherein said tibia stabilizing force-transfer assembly includes:

(1) a cammed surface secured to said first framework and positioned adjacent to said second framework, and (2) a force-transfer mechanism pivotally secured to said second framework, including a lever having first and second lever arms and an adjustable contact member and wherein said first lever arm is adjacent said cammed surface and carries said adjustable contact member adapted to bear against said cammed surface during relative knee movement, and a tibia retaining strap pivotally connected to said second lever arm whereby the force applied to said first lever arm through said cammed surface during knee movement is transferred by said second lever arm to said tibia retaining strip to prevent posterior dislocation of said tibia as the leg is brought into flexion.

10. The posterior orthotic knee brace system of claim 9 wherein said first and second frameworks each include depending side strips orthogonally connected to straps adapted to wrap around the respective upper and lower leg portions, said depending side strips being hingedly interconnected, said side strips of said first framework each being generally posteriorly displaced from said side strips of said second framework and wherein said side strips of said first framework further comprise a forwardly-extending offset end member having said cammed surface.

11. The posterior orthotic knee brace system of claim 10 wherein said side strips of said first framework are posteriorly displaced from said side strips of said second framework by said offset end members through which said frameworks are pivotably connected, and wherein said lever is generally L-shaped, said contact-member comprising a screw plunger threaded through said upper lever arm.

12. The posterior orthotic knee brace system of claim 11 wherein said tibia retaining strap is adapted to bear against the tibia to prevent its displacement during leg movement.

13. The posterior orthotic knee brace system of claim 12 wherein said cammed surface is located rearwardly of said second framework strips and wherein said lever arms also extend rearwardly of said second framework strips to treat posterior knee injuries.

14. The posterior orthotic knee brace system of claim 9 wherein said system includes a pair of said first and second side strips located one pair each on either side of said posterior orthotic knee brace system and wherein both pairs further include said force transfer mechanism.

* * * * *